United States Patent [19]

Cassou et al.

[11] Patent Number: 5,190,880
[45] Date of Patent: Mar. 2, 1993

[54] TUBE KNOWN AS STRAW, FOR CRYOGENICALLY PRESERVING BIOLOGICAL SAMPLES

[76] Inventors: Robert Cassou, "Les Camus" Sainte Montaine, 18700 Aubigny-sur-Nere; Maurice Cassou; Bertrand Cassou, both of 10 rue Georges Clémenceau, 61300 L'Aigle, all of France

[21] Appl. No.: 607,684

[22] Filed: Nov. 1, 1990

[51] Int. Cl.[5] .................. C12M 1/24; C12M 3/00
[52] U.S. Cl. .................................. 435/296; 435/1;
435/2; 435/284; 435/285; 435/286; 435/287;
435/290; 435/235.1; 422/102; 62/457.9;
606/20; 606/21; 606/22; 606/23; 606/24;
606/25; 606/26; 525/221
[58] Field of Search ............................. 435/1-2,
435/284-287, 290, 296, 235.1; 422/102;
62/457.9; 606/20-26; 525/221

[56] References Cited

U.S. PATENT DOCUMENTS

| | | | |
|---|---|---|---|
| 3,151,760 | 10/1964 | Cowley et al. | 62/457.9 |
| 3,404,134 | 10/1968 | Rees | 260/78.5 |
| 3,579,303 | 5/1971 | Pickering | 435/296 |
| 3,694,317 | 9/1972 | Scher | 435/296 |
| 4,117,881 | 10/1978 | Williams et al. | 435/1 |
| 4,262,494 | 4/1981 | Karow | 62/457.9 |
| 4,464,337 | 8/1984 | Zelman | 435/2 |
| 4,630,448 | 12/1986 | Bilstad et al. | 435/2 |
| 4,681,839 | 7/1987 | Swartz | 435/1 |
| 4,688,387 | 8/1987 | Conaway | 435/1 |
| 4,783,973 | 11/1988 | Angelier | 62/457.9 |
| 4,801,649 | 1/1989 | Statz | 525/221 X |
| 4,911,451 | 3/1990 | Sullivan et al. | 525/221 X |
| 4,983,515 | 1/1991 | Maley et al. | 435/2 |
| 5,026,342 | 6/1991 | Hammerstedt et al. | 435/2 X |
| 5,068,151 | 11/1991 | Nakamura | 525/221 X |

FOREIGN PATENT DOCUMENTS

| | | | |
|---|---|---|---|
| 2618452 | 1/1989 | France | . |
| 2651793 | 3/1991 | France | 435/296 |
| 0051086 | 4/1977 | Japan | 435/296 |

Primary Examiner—Robert J. Warden
Assistant Examiner—Stephanie Blythe
Attorney, Agent, or Firm—Perry Carvellas

[57] ABSTRACT

The tube, known as a straw, according to the invention, is conventional in its form, and is constituted by a rectilinear length of transparent tubular envelope. In the vicinity of a first end, the straw contains a sliding stopper with a quantity of powder gellable by hydration between two porous pads. The tubular envelope is extruded from an ionomer resin marketed under the brand name of Surlyn 8921. Ionomer resins have, above and below a transition zone extending from 45° C. to 60° C. approximately, states that are respectively thermofusible and crosslinked. Thus, the straw can be closed by fusion of the ends clamped by heated jaws, while presenting suitable properties of rigidity at ambient temperature. Furthermore, the ionomer resin used does not have an embrittlement temperature, so that it can be manipulated at cryogenic temperatures (77 K) without the need for taking any particular precautions. The filling and sealing of the straws can be automated, to ensure the safety of the operators.

9 Claims, 2 Drawing Sheets

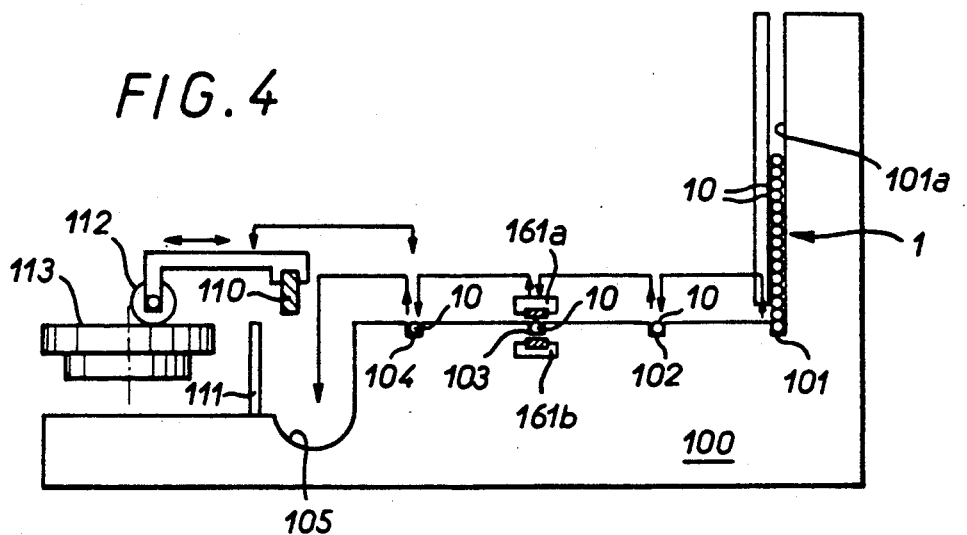
FIG. 4
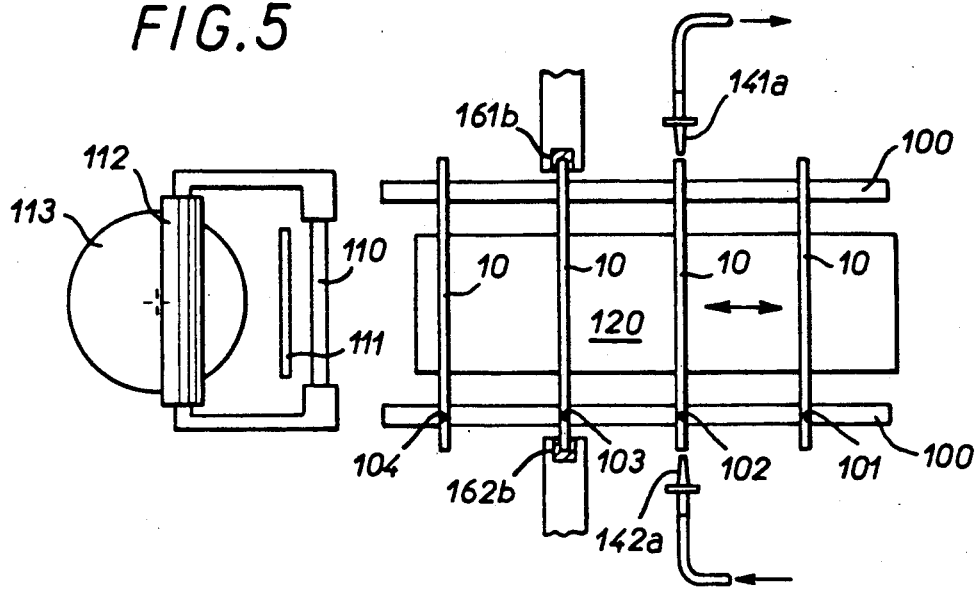
FIG. 5
FIG. 6A
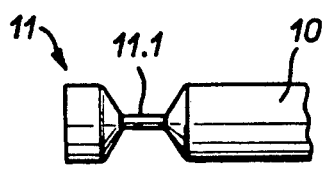
FIG. 7A
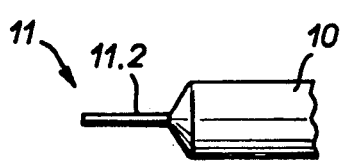
FIG. 8A
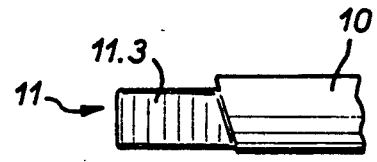
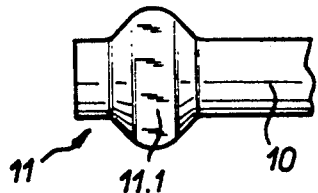
FIG. 6B
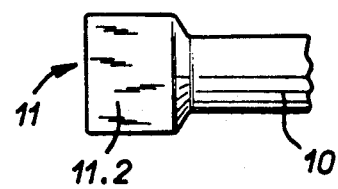
FIG. 7B
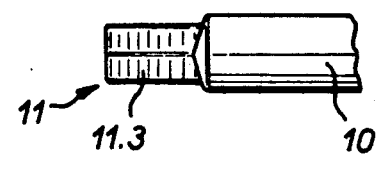
FIG. 8B

TUBE KNOWN AS STRAW, FOR CRYOGENICALLY PRESERVING BIOLOGICAL SAMPLES

BACKGROUND OF THE INVENTION

The invention relates to a tube, known as a straw, for cryogenically preserving biological samples, in particular viral cultures, formed by a length of tubular envelope made of biologically neutral, substantially transparent polymer material, provided with a seal at each of its two ends and including, in the vicinity of a first end, a sliding stopper comprising an aqueous gel between two pads made of porous elastic material.

The invention also relates to a process for filling a tube or straw of this type.

DESCRIPTION OF THE PRIOR ART

This type of straw constituted by a length of envelope twelve or so centimeters long and approximately three millimeters in diameter, with a wall thickness of several tenths of a millimeter, has long been known in the art: the sliding stopper, also known as a tripartite plug, was described in document FR-A-995 878 of Sep. 20, 1946. Since then, various improvement have been made thereto, these improvements relating essentially to the end seals, in conjunction with the polymer material from which the envelope is extruded. Indeed, the stoppering process has to provide efficient sealing, not present excessive risks of damage to the biological sample contained and it must be suitable, at least in certain applications, for the handling necessary for such applications (preservation and use of gametes, in vitro fertilization, etc.).

Furthermore, the choice of envelope material has been dictated by considerations of compatibility with biological substances, transparency and ease of forming. Practically speaking, all materials that include plasticizers liable to migrate will be rejected.

Document FR-A-2 128 374 describes a seal produced by ultrasonically welding straws of a material that is not specified. The welding is carried out between matching V-shaped jaws, one connected to the ultrasound generator and the other forming an anvil; in this way, a seal is obtained that is inscribed within the cylinder that corresponds to the tube on the outside.

Document FR-A-2 592 297 describes a process for stoppering by injecting a thermofusible material in the form of a paste inside the tube end; the straw is made of polyvinyl chloride and the thermofusible material is a mixture of a polyolefin and an ethylene and vinyl acetate copolymer.

Document FR-A-2 618 452 describes a straw stoppered, at the end opposite that adjoining the sliding stopper, by an elastomer plug capable of being pierced by a needle, and of remaining tight after the needle has been withdrawn. The elastomer plug is either inserted by force or formed in situ by vulcanizing a suitable composition.

Document FR-A-2 623 205 describes a straw for fertilization that does not comprise a sliding stopper and which is fitted at each end with a self-sealing elastomer plug.

Advances in microbiology have led to an increase in the use of such straws, in connection with work on sometimes rare biological samples, and often particularly in the case of dangerous viral cultures. It was becoming vital to review the design of the straw, particularly with regard to its end seals, on one hand to avoid the use of injection needles, capable of causing injury to the personnel having cause to manipulate them, and to facilitate the automation of sample filling and withdrawing operations and, on the other hand, to limit rigorously the risks of loss of tightness of the filled straws as a result of thermal shocks and stresses linked with freezing by immersion in liquid nitrogen, and rapid thawing out.

Although the straws currently used have a failure rate, under cryogenic conditions, that is acceptable for routine work, this failure rate becomes excessive insofar as the unusability of a filled straw can lead to the failure of a research programmme or the risks of infection due to the leakage of a sample take on a dramatic aspect.

SUMMARY OF THE INVENTION

The applicants have thus made it their aim to produce a tube or straw that would offer considerably increased reliability in cryogenic preservation, including in the sealing zones, and that could be filled and sealed easily in an automatic installation that would not necessitate manipulation by an operator.

The applicants indeed consider that they have achieved this objective in providing a tube known as a straw for the cryogenic preservation of biological samples, notably viral cultures, formed by a length of calibrated tubular envelope of biologically neutral, substantially transparent polymer material, provided with a seal at each of its two ends and including, in the vicinity of a first end, a sliding stopper comprising an aqueous gel between two pads of porous elastic material, characterized in that the polymer material is an ionomer resin, the end seals being formed by autogenously welding the tube over a limited axial extent.

The ionomer resins, formed through the association of an ethylene copolymer and a carboxyl acid with a metallic cation having the property of behaving, above a transition temperature zone, in the 40°-90° range, like a thermoplastic material, while below this transition zone, they behave like a crosslinked material, the metallic cations forming cross links between linear chains of copolymer. The transformation is reversible. The autogenous welding of the tube is simple and efficient, above the transition temperatures; the cooling after welding induces only very little internal stress, the setting of the resin by ionic crosslinking not being accompanied by large variations in volume.

Such ionomer resins are described in French patents 1,336,464, 1,355,608 and 1,430,478 filed by the company Dupont de Nemours on Aug. 28, 1962, Jan. 23, 1963 and Feb. 26, 1965 respectively. These resins are marketed under the brand name of "Surlyn", a registered trademark of Du Pont.

Most solids have a embrittlement temperature beneath which creep is practically inhibited. Thermoplastic polymer materials are, in general, very sensitive to cold embrittlement, particularly when they do not include a plasticizer. Ionomer resins themselves have very low embrittlement temperatures, always below 213 K, and for the most part less than 173 K. For certain "Surlyn" resins, it has not proved possible to demonstrate the existence of an embrittlement temperature.

It will be appreciated that the manipulation of conventional straws, cooled down to the temperature of the liquid nitrogen, 77 K, is delicate and does not lend itself easily to automation. Furthermore, if internal stresses persist in the welds, cracking can occur in the seal. Such difficulties are attenuated or disappear with the straws according to the invention.

The crosslinked structure of "Surlyn" resins at ambient temperature gives the straws advantageous mechanical properties; the straws have no tendency to creep under their own weight and remain rectilinear. The positioning of the ends of the straws, placed on an appropriate support, will be precise and the introduction of a needle or of a conical nozzle for filling purposes is thus facilitated, without necessitating any intervention by operators, even occasionally.

It will be noted that the conventional straws have long given satisfaction, the losses of tightness by breakage or cracking due to embrittlement appearing compatible with the acceptable rate of errors and handling accidents that are inevitable. It is only recently that the need to lower the thresholds for acceptable wastage rates has led the Applicant to analyse the possible causes of accidents, with a view to reducing these accidents. It can be supposed that, originally, the straw manufacturers chose the materials that were usual in the biological laboratory materials industry and the behaviour of which, with regard to biological samples and to cryogenic applications, was known.

Of course, "Surlyn" resins possess suitable qualities of transparency and biological neutrality. It will be noted in passing that these resins accept marking inks, which makes it possible to identify the filled straws without any risk of error.

Preferably, the ionomer resin will be of the type marketed under the name of "Surlyn" 8921. This resin includes a metallic sodium cation, and it did not prove possible to determine its embrittlement temperature. In relation to the transition zone, the temperature of deflection under a load of 0.46 MPa is 45° C., the VICAT temperature (speed B) is 58° C., the melting temperature is 84° C., and the solidification temperature is 52° C.

According to another aspect, the invention provides a process for filling a tube known as a straw for cryogenically preserving biological samples, in particular viral cultures, constituted by a length of calibrated tubular envelope of biologically neutral, substantially transparent polymer material, a process wherein a sliding stopper is installed in the vicinity of a first end of the tube by successively inserting a first porous elastic pad, a quantity of powder capable of gelling upon coming into contact with an aqueous phase, and then a second porous elastic pad, the stopper being pushed beyond a zone of the tube allocated for sealing the first end, the biological sample is injected into the tube, previously sterilized, through the second end and beyond a zone allocated for sealing this end, while the atmosphere of the tube is discharged through the stopper and the first end until the aqueous phase, passing through the first pad, causes the gelling of the powder and thus ensures the tightness of the stopper, characterized in that the tubular envelope being constituted by an ionomer resin, the ends of the tube are sealed by crushing the tube in the zones allocated in such a way as to apply one against the other two portions of the internal peripheral layer of the tube, and by raising the temperature of at least these two portions sufficiently for them to fuse.

The use of an ionomer resin to form the tubular envelope, apart from the specific advantages imparted by the resin to the tube or straw for cryogenically preserving biological samples, enables the sealing to be carried out simply and in a way that can easily be automated, without any risk of damaging the contents by overheating the sample, at the same time ensuring the sterilization of the weld joint properly speaking, on account of the temperature at which the autogenous welding is carried out (in the 90° C.-110° C. range).

Further features and advantages of the invention will emerge, moreover, from the following description, given by way of example, with reference to the annexed drawings.

BRIEF DESCRIPTION OF THE DRAWINGS

FIG. 4 is a schematic elevation view of a straw filling and sealing unit;

FIG. 5 is a top view of the unit shown in FIG. 4;

FIGS. 6A and 6B are views in two orthogonal planes of a first type of seal;

FIGS. 7A and 7B are analogous representations of a second type of seal;

FIGS. 8A and 8B are analogous representations of a third type of seal.

DESCRIPTION OF THE PREFERRED EMBODIMENT

Figure 1:
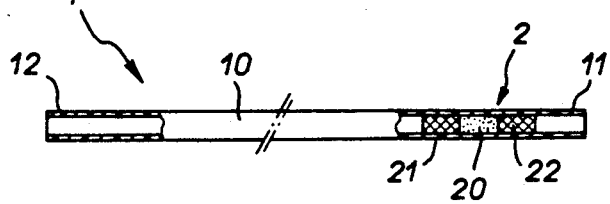
FIG. 1 is a view, partially cut away, of a tube or straw according to the invention.

According to the form of embodiment chosen and represented in FIG. 1, a tube 1, or so-called straw, is provided for the cryogenic preservation, at the temperature of liquid nitrogen, i.e. 77 K, of biological samples, in particular viral cultures. It is designed to ensure high security against the leakage of samples, despite the stresses brought about by the low temperatures, and to permit automatic handling, particularly for filling, in order to minimize the risks of infection for the user personnel. This tube, 1, comprises a tubular envelope 10, produced by extrusion of an ionomer resin marketed by the company Dupont de Nemours under the brand name of "Surlyn" 8921. The properties of this resin, and in particular the absence of an embrittlement point at 77 K and above, have been mentioned earlier.

The tube has a length, before filling, of 90 mm, an outside diameter of approximately 3 mm and an inside diameter of 2.5 mm.

Conventionally, tube 1 contains a sliding stopper 2, in the vicinity of an end 11, which will be termed the first end. This stopper comprises, on either side of a quantity of polyvinyl alcohol powder 20 that is hydrophilous and capable of gelling in contact with an aqueous phase, two porous pads 21 and 22, constituted by sections of braided cotton strip. The length of the stopper is approximately 18 mm, each of the elements 20, 21 and 22 occupying a length of approximately 6 mm. The useful internal volume is 250 $\mu$l. The calibration of the tubular envelope 10 at extrusion, and in particular the calibration of the internal section, makes it possible to reproduce the inside diameter.

Figure 2A:
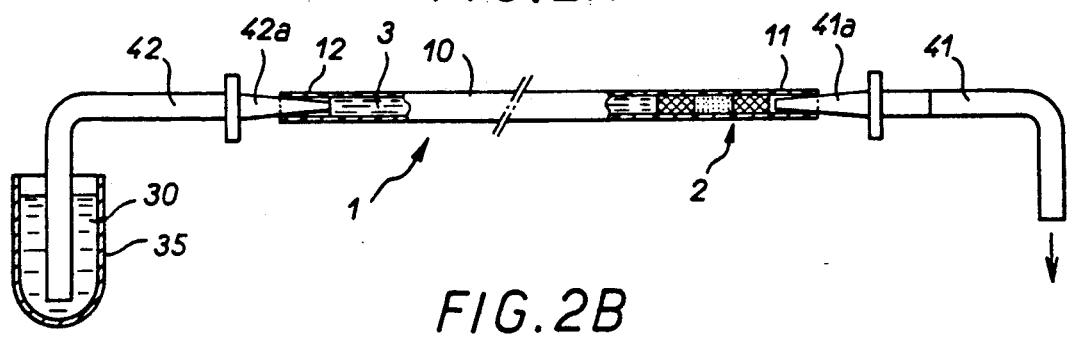
FIG. 2A is a view of a first process for filling a straw.

The filling of the straw is illustrated in FIG. 2A. Tube 1, which has been previously sterilized, is held between two frustoconical cannulas 41a and 42a, which penetrate respectively the ends 11 and 12; the frustoconical shape of cannulas 41a and 42a, combined with a force pressing them towards one another, ensures the tightness of the connection. Cannula 41a, at the end of a tube 41, is connected to a vacuum reservoir, while cannula 42a is at the end of a tube 42 which dips into a test tube 35 containing the biological sample 30.

The atmosphere of the tube 1 is discharged through the sliding stopper 2, and the biological sample 30 is drawn in through the tube 42 and penetrates the tubular envelope 10 until it reaches the stopper 2. Biological sample 3 infiltrates pad 21 and hydrates the powder 20, which forms a gel that is impermeable as a result of hydration. The filling is thus halted. When cannulas 41a and 42a are withdrawn, biological sample 3 remains in the form of a continuous column and the end 12, over the depth of penetration of cannula 42a, does not contain any sample and remains available for subsequent sealing, like end 11, which has not been reached by the sample.

It will be appreciated that the relative rigidity of tube 1 made of "Surlyn" at ambient temperature, permits the longitudinal compression of envelope 10 required for the purpose of tightness, and that the maintaining of a precise shape without flexion, below the transition zone of the ionomer resin, permits the precise, automatic introduction of cannulas 41a and 42a into ends 11 and 12 of straw 1.

Figure 2B:
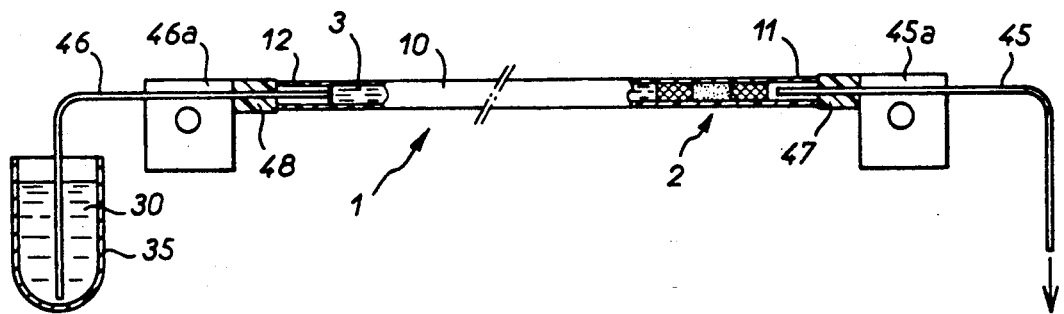
FIG. 2B is a view of a filling variant.

The device represented in FIG. 2B is analogous to that of FIG. 2A, with the exception, however, that tubes 41 and 42 are replaced by capillary tubes 45 and 46, fixed in clamps 45a and 46a. Tightness between tubes 45 and 46 and ends 11 and 12 is ensured by means of elastomer plugs 47 and 48, fitted onto capillary tubes 45 and 46, and abutting against the edges of ends 11 and 12 of straw 1. The filling process remains unchanged. It will be noted, however, that the capillary tube 46 penetrates end 12 of straw 1 deeply enough for this end 12 to remain empty over a length corresponding substantially to the depth of insertion of pad 22 into end 11.

Figure 3A:
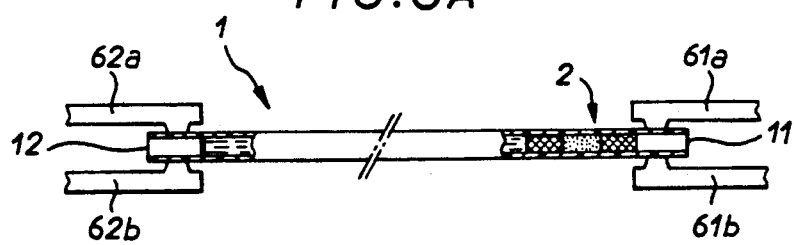
FIG. 3A illustrates a process for sealing a straw.

Straw 1, filled with biological sample 3, is then sealed as illustrated in FIG. 3A.

The ends 11 and 12 are clamped between pairs of jaws 61a, 61b; 62a, 62b until the tubular envelope has been crushed sufficiently for the opposite portions of the internal surfaces of ends 11 and 12 to come into contact. The pairs of jaws 61a, 61b; 62a, 62b are heated to a temperature such that the ionomer resin melts between the jaws and the opposite portions in contact fuse together.

It will be remembered that the ionomer resin chosen has a melting point of 84° C. and that the zone of transition between the thermofusible state and the crosslinked state is between 45° C. and 60° C., approximately.

Figure 3B:
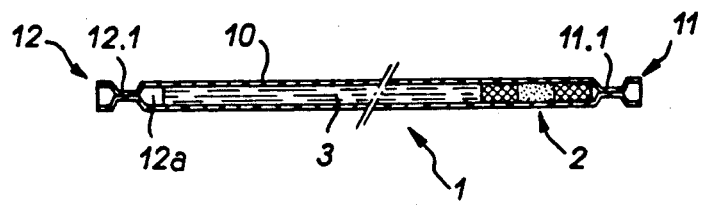
FIG. 3B is a longitudinal cross-section of a sealed and filled straw.

After sealing, straw 1 has substantially the appearance illustrated in FIG. 3B, with, at the two ends 11 and 12, flattened sealing zones 11.1 and 12.1. It will be noted that, between sealing zone 12.1 and the end of column 3 of biological sample, there remains a bubble of gas 12a. Apart from the fact that, as is known, the bubble of gas 12a prevents failure of the straw, the freezing of the sample being accompanied by an increase in volume, at the time of sealing, bubble 12a prevents contact between the heated zone 12.1 and the biological sample, which could otherwise be damaged.

It will be noted that, on the other hand, if traces of biological sample had extended between the ends 11 and 12 of the straw, the organic materials of these traces would be substantially destroyed at the melting temperature of the resin, with sterilization of the accessible ends.

Referring now to FIGS. 4 and 5, which show a filling unit, it can be seen that unit 100 comprises notches 101, 102, 103 and 104, for positioning the straws. A transport member 120 periodically comes and raises the straws and then displaces them towards the left, by one interval between notches, lowers them into the corresponding notch and withdraws to recommence transport again, after a chosen period has elapsed.

The sterilized straws are placed in the vertical loader 101a, with the lowest straw engaging in the slot 101 or loading slot. After transfer to slot 102, the filling position, cannulas 141a and 142a are brought towards one another to be introduced into the ends of the straw, filling taking place as described with reference to FIG. 2A.

After filling, straw 10 is transferred to slot 103, where it is welded by heated jaws 161a, 161b; 162a, 162b by means of the process described with reference to FIG. 3A.

After this, straw 10 is transferred to slot 104, where it undergoes marking. A marker 111, bearing characters in relief, is inked by the passage of an inking roll, coupled to a rotating inking plate 113. A transfer pad 110 receives, in a recoil movement, the mark formed by marker 111 and, in a forward movement, transfers the mark to straw 10 in slot 104.

Upon the following action of the transport member 120, straw 10 is discharged into channel 105.

It will be appreciated that all these operations are carried out without any intervention by a human operator.

It will be noted that the marking could, a priori, be a secondary operation, without any risk to a human operator. However, it is important for this marking to take place just after the straw has been personalized, to avoid any possibility of error. Moreover, this marking would have been a far more complex undertaking if the material of which the straw is made were not capable of fixing the marking ink.

We refer now to FIGS. 6 to 8, each composed of a FIG. A, viewed parallel to the direction in which the jaws move towards each other, and of a FIG. B.

FIGS. 6A and 6B show the form of seal 11.1 obtained by clamping between flat, narrow jaws and which leaves the edge of straw envelope 10 intact. This form will be the usual one.

FIGS. 7A and 7B show a seal 11.2 in the form of a blade, obtained by clamping between plane jaws that grip the straw by its end. This form may be preferred for the ease of gripping the straw; moreover, it eliminates the end cavity of seal 11.1.

FIGS. 8A and 8B show a V-shaped seal 11.3, analogous to the one described in document FR-A-2 128 374. This form, which is the result of clamping between two V-shaped jaws, one projecting and the other re-entrant, has the advantage that the seal is completely contained inside the cylinder that corresponds to the outer surface of the straw, so that it is easier for the straw to be fixed in a chuck.

Of course, it may be appropriate to shape the two straw end seals differently, for reasons of convenience. Indeed, other forms of seal are conceivable.

It will be appreciated, of course, that, in order to recover the biological sample for use, the ends 11 and 12 are sectioned flush with the underformed zones that are beyond the seals, and that the sample is expelled by pushing the sliding stopper mechanically or pneumatically.

It goes without saying that the invention is not limited to the examples described, but encompasses any variants, within the scope of the claims.

What we claim is:

1. A tube for cryogenic preservation of biological specimens, in particular viral cultures, comprising a tubular envelope of predetermined length having opposed ends, said tubular envelope being made of a biologically neutral, substantially transparent polymer material, a seal being defined at each end of said tubular envelope, a sliding stopper being located axially inwardly of and proximate to one of said ends and comprising aqueous gel disposed between two pads of porous elastic, said polymer material being an ionomer resin having an embrittlement temperature less than or equal to 77 K, and the end seals comprising autogenic welds.

2. A tube according to claim 1, wherein said ionomer resin is derived from ethylene methacrylic acid copolymers.

3. A tube according to claim 1, wherein said ionomer resin comprises Surlyn 8921 (Surlyn is a registered trademark of DuPont) ionomer resin.

4. A tube according to claim 1, wherein said tubular envelope has an outer diameter, at least one of said ends of said tubular envelope having two planar, parallel outer faces extending perpendicularly to the axis thereof, the width of the faces being greater than the outer diameter of the tubular envelope.

5. A tube according to claim 1, wherein said tubular envelope has an outer diameter, the at least one of said ends of said tubular envelope having V-shaped faces, one of the faces being a convex V-shaped face and the other being a concave V-shaped face, the width of the faces being less than the outer diameter of the tubular envelope.

6. A tube according to claim 1, wherein the tube contains a predetermined volume of a biological specimen, a gas bubble being formed between the biological sample and the seal at the end of said tubular envelope, remote from the sliding stopper.

7. A tube for cryogenic preservation of biological specimens, in particular viral cultures, comprising a tubular envelope of predetermined length having opposed ends, said tubular envelope being made of a biologically neutral, substantially transparent polymer material, a seal being defined at each end of said tubular envelope, a sliding stopper being located axially inwardly of and proximate to one of said ends and comprising aqueous gel disposed between two pads of porous elastic, said polymer material being an ionomer resin having an embrittlement temperature less than or equal to 77 K, a melting temperature of 85° C. and a solidification temperature of 52° C., and the end seals comprising autogenic welds.

8. A tube according to claim 7, wherein said ionomer resin is derived from ethylene methacrylic acid copolymers.

9. A tube according to claim 7, wherein said ionomer resin has a temperature of deflection under a load of 0.46 MPa of 45° C.

* * * * *